United States Patent [19]

Pitteloud

[11] Patent Number: 5,670,642
[45] Date of Patent: Sep. 23, 1997

[54] HALS PHOSPHORAMIDES AS STABILISERS

[75] Inventor: Rita Pitteloud, Praroman, Switzerland

[73] Assignee: Ciba-Geigy Corporation, Tarrytown, N.Y.

[21] Appl. No.: 572,990

[22] Filed: Dec. 15, 1995

[30] Foreign Application Priority Data

Dec. 22, 1994 [CH] Switzerland .................. 3898/94

[51] Int. Cl.$^6$ ........................................ C07F 9/32
[52] U.S. Cl. ........................................ 546/22
[58] Field of Search ................................. 546/22

[56] References Cited

U.S. PATENT DOCUMENTS

| | | | |
|---|---|---|---|
| 4,301,061 | 11/1981 | Rasberger | 260/45.8 N |
| 4,322,527 | 3/1982 | Rasberger | 544/157 |
| 4,386,204 | 5/1983 | Rasberger | 546/21 |
| 4,409,346 | 10/1983 | Rasberger | 524/83 |

FOREIGN PATENT DOCUMENTS

| | | |
|---|---|---|
| 0020297 | 12/1980 | European Pat. Off. . |
| 0149259 | 7/1985 | European Pat. Off. . |
| 0312915 | 4/1989 | European Pat. Off. . |
| 0349895 | 1/1990 | European Pat. Off. . |
| 0389430 | 9/1990 | European Pat. Off. . |
| 0540025 | 5/1993 | European Pat. Off. . |
| 0569328 | 11/1993 | European Pat. Off. . |
| 4306747 | 9/1993 | Germany . |
| 2087399 | 5/1982 | United Kingdom . |
| 2250990 | 6/1992 | United Kingdom . |

OTHER PUBLICATIONS

Allen, et al. Polymer Degradation and Stability, 46, (1994), 75–84.
J. Prakt. Chem. 334 (1992) pp. 333–349.
Beilstein EII, Band 22, S. 321 (1953).
J.D.C. vol. 27, 1695–1703 (1962).
Plastics Additives Handbook, 3rd Ed. p. 47, Hanser München 1990.

Derwent Abstr. 93–296322/38.
Derw. Abst. 93–296322 [38] of De. 4,306,747.

Primary Examiner—Matthew V. Grumbling
Assistant Examiner—Michael Buckman
Attorney, Agent, or Firm—Michele Kovaleski; David R. Crichton

[57] ABSTRACT

The invention relates to novel compounds of formula I

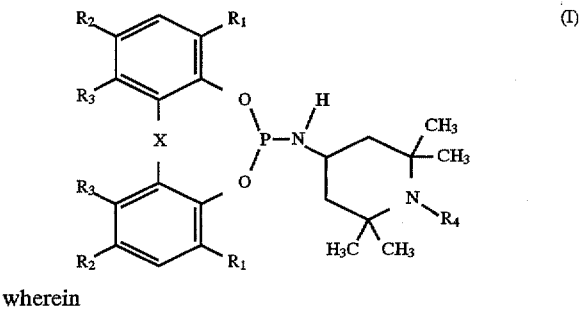

wherein

X is a direct bond, sulfur or —$CHR_5$—, $R_1$ is hydrogen, $C_1$–$C_{25}$ alkyl, unsubstituted or $C_1$–$C_4$alkyl-substituted $C_5$–$C_8$cycloalkyl; unsubstituted or $C_1$–$C_4$alkyl-substituted $C_5$–$C_8$cycloalkenyl; unsubstituted or $C_1$–$C_4$alkyl-substituted phenyl; $C_7$–$C_9$phenylalkyl or —$CH_2$—S—$R_6$; $R_2$ is hydrogen, $C_1$–$C_{25}$alkyl, $C_2$–$C_{24}$alkenyl, unsubstituted or $C_1$–$C_4$alkyl-substituted $C_5$–$C_8$cycloalkyl; unsubstituted or $C_1$–$C_4$alkyl-substituted $C_5$–$C_8$cycloalkenyl; unsubstituted or $C_1$–$C_4$alkyl-substituted phenyl; $C_7$–$C_9$-phenylalkyl or —$CH_2$S—$R_6$; $R_3$ is hydrogen or methyl; $R_4$ is $C_1$–$C_8$alkyl, O·, OH, NO, —$CH_2$CN, $C_1$–$C_{18}$alkoxy, $C_5$–$C_{12}$cycloalkoxy, $C_3$–$C_6$alkenyl, $C_3$–$C_6$alkynyl, $C_1$–$C_{87}$acyl, $C_7$–$C_9$phenylalkyl which is unsubstituted or substituted at the phenyl ring by $C_1$–$C_4$alkyl; $R_5$ is hydrogen or $C_1$–$C_8$alkyl; and $R_6$ is $C_1$–$C_{20}$alkyl, as stabilisers for protecting organic materials against oxidative, thermal or light-induced degradation.

18 Claims, No Drawings

HALS PHOSPHORAMIDES AS STABILISERS

The present invention relates to novel HALS phosphoramides, to compositions comprising an organic material, preferably a polymer, and the novel HALS phosphoramides, and to the use thereof for stabilising organic materials against oxidative, thermal or light-induced degradation.

Organic phosphites, phosphonites and phosphoramides are known in the art as co-stabilisers, secondary antioxidants and processing stabilisers, inter alia for polyolefins. Examples of such known phosphite stabilisers will be found in R. Gächter/H. Müller (Ed.), Plastics Additives Handbook, 3rd Ed., p. 47, Hanser, Munich 1990, and in EP-A-356 688.

Hindered amines, including in particular compounds containing 2,2,6,6-tetramethylpiperidyl groups, preferably find utility as light stabilisers (hindered amine light stabilisers; HALS).

Phosphites, phosphonites or phosphoramides containing HALS structural units are disclosed, inter alia, in T. K önig et al, J. prakt. Chem. 334, 333–349 (1992), in EP-A-0 020 297, U.S. Pat. No. 4,322,527, U.S. Pat. No. 4,386,204, U.S. Pat. No. 4,409,346, EP-A-0 149 259, EP-A-0 389 430, EP-A-0 540 025 and DE-A-4 306 747.

The known stabilisers do not in all respects meet the exacting requirements which a stabiliser must fulfill, in particular with respect to storage stability, water absorption, sensitivity to hydrolysis, processing stability, discolouration, volatility, migration stability, compatibility and light stability. There is therefore still a need to provide effective stabilisers for organic materials which are susceptible to oxidative, thermal and/or light-induced degradation.

It has now been found that a selected group of such HALS phosphoramides is particularly suitable for use as stabilisers for organic materials which are susceptible to oxidative, thermal or light-induced degradation. The suitability of said compounds as processing stabilisers for synthetic polymers is to be particularly highlighted.

Accordingly, the present invention relates to compounds of formula I

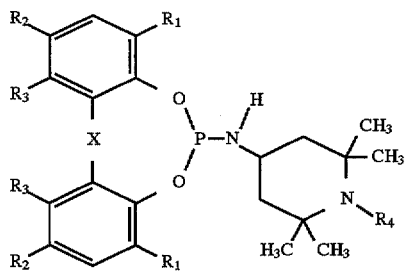

wherein

X is a direct bond, sulfur or —CHR$_5$—,

R$_1$ is hydrogen, C$_1$–C$_{25}$alkyl, unsubstituted or C$_1$–C$_4$alkyl-substituted C$_5$–C$_8$cycloalkyl; unsubstituted or C$_1$–C$_4$alkyl-substituted C$_5$–C$_8$cycloalkenyl; unsubstituted or C$_1$–C$_4$alkyl-substituted phenyl; C$_7$–C$_9$phenylalkyl or —CH$_2$—S—R$_6$, R$_2$ is hydrogen, C$_1$–C$_{25}$alkyl, C$_2$–C$_{24}$alkenyl, unsubstituted or C$_1$C$_4$alkyl-substituted C$_5$–C$_8$cycloalkyl; unsubstituted or C$_1$–C$_4$alkyl-substituted C$_5$–C$_8$cycloalkenyl; unsubstituted or C$_1$–C$_4$alkyl-substituted phenyl; C$_7$–C$_9$phenylalkyl or —CH$_2$—S—R$_6$, R$_3$ is hydrogen or methyl, R$_4$ is C$_1$–C$_8$alkyl, O·, OH, NO, —CH$_2$CN, C$_1$–C$_{18}$alkoxy, C$_5$–C$_{12}$cycloalkoxy, C$_3$–C$_6$alkenyl, C$_3$–C$_6$alkynyl, C$_1$–C$_8$acyl, C$_7$–C$_9$phenylalkyl which is unsubstituted or substituted at the phenyl ring by C$_1$–C$_4$alkyl, R$_5$ is hydrogen or C$_1$–C$_8$alkyl, and R$_6$ is C$_1$–C$_{20}$alkyl.

Alkyl of up to 25 carbon atoms is a branched or unbranched radical, typically methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,3,3-tetramethylbutyl, 1-methylheptyl, 3-methylheptyl, n-octyl, 2-ethylhexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, eicosyl or docosyl. One of the preferred meanings of R$_1$ and R$_2$ is C$_1$–C$_{18}$alkyl, preferably C$_1$–C$_{12}$alkyl, e.g. C$_1$–C$_8$alkyl. A particularly preferred meaning of R$_1$ and R$_2$ is C$_1$–C$_4$alkyl, most preferably tert-butyl. A preferred meaning of R$_4$ is C$_1$–C$_6$alkyl, preferably C$_1$–C$_4$alkyl, e.g. methyl. A particularly preferred meaning of R$_5$ is C$_1$–C$_{16}$alkyl, preferably C$_1$–C$_4$alkyl, e.g. methyl. A particularly preferred meaning of R$_6$ is C$_1$–C$_{12}$alkyl, preferably C$_1$–C$_{10}$alkyl, e.g. C$_1$–C$_8$alkyl.

Alkenyl of 2 to 24 carbon atoms is a branched or unbranched radical, typically vinyl, propenyl, 2-butenyl, 3-butenyl, isobutenyl, n-2,4-pentadienyl, 3-methyl-2-butenyl, n-2-octenyl, n-2-dodecenyl, isododecenyl, oleyl, n-2-octadecenyl or n-4-octadecenyl. A particularly preferred meaning of R$_2$ is alkenyl of 2 to 18, preferably 3 to 12, e.g. 3 to 10, carbon atoms. A particularly preferred meaning of R$_4$ is propenyl.

Unsubstituted or C$_1$–C$_4$alkyl-substituted C$_5$–C$_8$cycloalkyl, which preferably contains 1 to 3, more particularly 1 or 2, branched or unbranched alkyl groups, is typically cyclopentyl, methylcyclopentyl, dimethylcyclopentyl, cyclohexyl, methylcyclohexyl, dimethylcyclohexyl, trimethylcyclohexyl, tert-butylcyclohexyl, cycloheptyl or cyclooctyl. Cyclohexyl is preferred.

Unsubstituted or C$_1$–C$_4$alkyl-substituted C$_5$–C$_8$cycloalkenyl, which preferably contains 1 to 3, more particularly 1 or 2, branched or unbranched alkyl groups, is typically cyclopentenyl, methylcyclopentenyl, dimethylcyclopentenyl, cyclohexenyl, methylcyclohexenyl, dimethylcyclohexenyl, trimethylcyclohexenyl, tert-butylcyclohexenyl, cycloheptenyl or cyclooctenyl. Cyclohexenyl is preferred.

C$_7$–C$_9$phenylalkyl which is unsubstituted or substituted at the phenyl radical by C$_1$–C$_4$alkyl and which preferably contains 1 to 3, more particularly 1 or 2, branched or unbranched alkyl groups is typically benzyl, α-methylbenzyl, α,α-dimethylbenzyl, 2-phenylethyl, 2-methylbenzyl, 3-methylbenzyl, 4-methylbenzyl, 2,4-dimethylbenzyl, 2,6-dimethylbenzyl or 4-tert-butylbenzyl. Benzyl is preferred.

C$_1$–C$_4$alkyl-substituted phenyl, which preferably contains 1 to 3, more particularly 1 or 2, alkyl groups, is typically o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl.

Alkoxy of up to and including 18 carbon atoms is a branched or unbranched radical, typically methoxy, ethoxy, propoxy, isopropoxy, n-butoxy, isobutoxy, pentyloxy, isopentyloxy, hexyloxy, heptyloxy, octyloxy, decyloxy, tetradecyloxy, hexadecyloxy or octadecyloxy. A preferred meaning of R$_4$ is alkoxy of 4 to 18, preferably 6 to 12, carbon atoms.

Cycloalkoxy of 5 to 12 carbon atoms is typically cyclopentyloxy, cyclohexyloxy, cycloheptyloxy, cyclooctyloxy, cyclodecyloxy or cyclododecyloxy. One of the preferred meanings of $R_4$ is $C_5$–$C_8$cycloalkoxy. Cyclopentyloxy and cyclohexyloxy are particularly preferred.

Alkynyl of 3 to 6 carbon atoms is a branched or unbranched radical, typically propynyl (propargyl) —$CH_2$—$C\equiv CH$ ), but-2-ynyl or but-3-ynyl.

Acyl of 1 to 8 carbon atoms is typically formyl, acetyl, propionyl, butyryl, pentanoyl, hexanoyl, heptanoyl, octanoyl, benzoyl, acryloyl or crotonyl. $C_1$–$C_8$alkanoyl, $C_3$–$C_8$alkenoyl or benzoyl are preferred, and acetyl is particularly preferred.

Preferred compounds of formula I are those wherein $R_1$ is hydrogen, $C_1$–$C_{18}$alkyl, $C_5$–$C_8$acycloalkyl, $C_5$–$C_8$cycloalkenyl, phenyl, $C_7$–$C_9$phenylalkyl or —$CH_2$—S—$R_6$, $R_2$ is hydrogen, $C_1$–$C_{18}$alkyl, $C_2$–$C_8$alkenyl, $C_5$–$C_8$cycloalkyl, $C_5$–$C_8$cycloalkenyl, phenyl, $C_7$–$C_9$phenylalkyl or —$CH_2$—S—$R_6$, $R_4$ is $C_1$–$C_4$alkyl, $C_4$–$C_{18}$alkoxy, $C_5$–$C_8$cycloalkoxy, allyl, propargyl, acetyl or benzyl, $R_5$ is hydrogen or $C_1$–$C_6$alkyl, and $R_6$ is $C_1$–$C_{12}$alkyl.

Other preferred compounds of formula I are those wherein $R_1$ and $R_2$ are each independently of the other hydrogen, $C_1$–$C_{12}$alkyl, cyclohexyl, phenyl or benzyl.

Also preferred are compounds of formula I, wherein $R_4$ is $C_1$–$C_4$alkyl, $C_4$–$C_{18}$alkoxy, $C_5$–$C_8$cycloalkoxy, allyl, propargyl, acetyl or benzyl.

Particularly preferred compounds of formula I are those wherein $R_4$ is $C_1$–$C_4$alkyl.

Compounds of formula I meriting particular interest are those wherein

X is a direct bond or —$CHR_5$, $R_1$ is $C_1$–$C_4$alkyl, cyclohexyl or phenyl, $R_2$ is $C_1$–$C_4$alkyl, cyclohexyl or phenyl, $R_3$ is hydrogen, $R_4$ is $C_1$–$C_4$alkyl, allyl or benzyl, and $R_5$ is hydrogen or $C_1$–$C_4$alkyl.

Very particularly preferred compounds of formula I are those wherein

X is a direct bond or —$CHR_5$, $R_1$ is $C_1$–$C_4$alkyl, $R_2$ is $C_1$–$C_4$alkyl, $R_3$ is hydrogen, $R_4$ is methyl, and $R_5$ is hydrogen or methyl.

The novel compounds of formula I may be prepared in per se known manner.

The invention furthermore relates to a preferred process for the preparation of compounds of formula I, which comprises reacting a compound of formula II

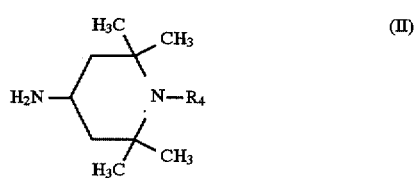

(II)

wherein $R_4$ has the given meaning, with a cyclic halophosphite of formula III

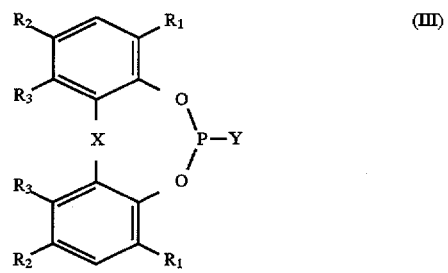

(III)

wherein X, $R_1$, $R_2$ and $R_3$ have the given meanings, and Y is chloro, bromo or iodo.

It is preferred to use the compounds of formula III, wherein Y is chloro.

The reaction is carried out in the melt or in the presence of a suitable organic, polar or nonpolar aprotic solvent. This reaction is preferably carried out in the presence of a base in the temperature range from –20° C. to the boiling point of the solvent, more particularly from 20° to 150° C.

Bases, such as amines, may simultaneously also be used as solvent. The compounds of formula II may also additionally be used as bases.

The base can be used in different amounts, from catalytic through stoichiometric amounts up to an excess of several times the molar amount with respect to the compounds of formula II or the compounds of fomula III. The hydrogen halide formed during the reaction is converted with the base, when used, into a halide, which can then be removed by filtration and/or washing with a suitable aqueous or solid phase. A second, water-immiscible, solvent may also be used in this case. The products are expediently isolated by evaporating the organic phase and drying the residue.

Suitable solvents for carrying out the reaction include hydrocarbons (typically mesitylene, toluene, xylene, hexane, pentane or other petroleum ether fractions), halogenated hydrocarbons (typically di- or trichloromethane, 1,2-dichloroethane, 1,1,1-trichloroethane or chlorobenzene), ethers (typically diethyl ether, dibutyl ether or tetrahydrofuran), ketones (typically acetone, ethyl methyl ketone, diethyl ketone, methyl propyl ketone or cyclohexanone), and also acetonitrile, butyl acetate, dimethyl formamide, dimethyl sulfoxide or N-methylpyrrolidone.

Suitable bases include primary, secondary and, preferably, tertiary amines (typically trimethylamine, triethylamine, tributylamine, N,N-dimethylaniline, N,N-diethylaniline or pyridine), alcoholates (e.g. sodium methylate), alkali metal hydroxides (e.g. sodium hydroxide or potassium hydroxide), or alkali metal carbonates (e.g. sodium carbonate or potassium carbonate). Tertiary amines are particularly preferred, in particular triethylamine.

The preparation of the compounds of formulae II and III is known.

The 4-aminopiperidines of formula II are known or can be prepared by the known methods described, inter alia, in Beilstein EII, Vol. 22, page 321 (1953) or by W. B. Lutz et al., Journal of Organic Chemistry Vol. 27, 1695–1703 (1962).

The cyclic halophosphites of formula III are known or can be prepared by the known methods described, inter alia, in GB-A-2 250 990, EP-A-0 540 025, EP-A-0 349 895 or EP-A-0 312 915.

The novel compounds of formula I are suitable for stabilising organic materials against oxidative, thermal or light-induced degradation.

Illustrative examples of such materials are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (uncrosslinked or crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), branched low density polyethylene (BLDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium (III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

5. Polystyrene, poly(p-methylstyrene), poly(α-methylstyrene).

6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with diglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyether imides, polyester imides, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.

20. Polysulfones, polyether sulfones and polyether ketones.

21. Crosslinked polymers derived from aldehydes on the one hand and phenols, ureas and melamines on the other hand, such as phenol/formaldehyde resins, urea/formaldehyde resins and melamine/formaldehyde resins.

22. Drying and non-drying alkyd resins.

23. Unsaturated polyester resins derived from copolyesters of saturated and unsaturated dicarboxylic acids with polyhydric alcohols and vinyl compounds as crosslinking agents, and also halogen-containing modifications thereof of low flammability.

24. Crosslinkable acrylic resins derived from substituted acrylates, for example epoxy acrylates, urethane acrylates or polyester acrylates.

25. Alkyd resins, polyester resins and acrylate resins crosslinked with melamine resins, urea resins; isocyanates, isocyanurates, polyisocyanates or epoxy resins.

26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

27. Natural polymers such as cellulose, rubber, gelatin and chemically modified homologous derivatives thereof, for example cellulose acetates, cellulose propionates and cellulose buryrates, or the cellulose ethers such as methyl cellulose; as well as rosins and their derivatives.

28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPOF/HIPS, PPO/PA 6.6 and copolymers, PA/HDPE, PA/PP, PA/PPO, PBT/PC/ABS or PBT/PET/PC.

29. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

30. Aqueous emulsions of natural or synthetic rubber, e.g. natural latex or latices of carboxylated styrene/butadiene copolymers.

Accordingly the invention also relates to compositions comprising (a) an organic material susceptible to oxidative, thermal or light-induced degradation, and (b) at least one compound of formula I.

The organic materials to be protected are preferably natural, semi-synthetic or, more particularly, synthetic polymers. Thermoplastic polymers are particularly preferred, more particularly PVC or polyolefins, most preferably polyethylene and polypropylene.

To be particularly highlighted is the action of the novel compounds against thermal and oxidative degradation, in particular when subjected to heat, as in the processing of thermoplasts. The novel compounds are thus admirably suited for use as processing stabilisers.

The compounds of formula I are preferably added to the material to be stabilised in amounts of 0.01 to 10%, typically of 0.01 to 5%, preferably of 0.025 to 3%, more preferably of 0.025 to 1%, based on the weight of the organic material to be stabilised.

In addition to the compounds of formula I, the novel compositions may contain further co-stabilisers, typically as the following:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-($\alpha$-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1' -yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocopherols, for example $\alpha$-tocopherol, $\beta$-tocopherol, $\lambda$-tocopherol, $\delta$-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)-amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of β-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo-[2.2.2]octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl) propionic acid, e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tertbutyl-4-hydroxyphenylpropionyl)hydrazine.

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4'-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- und dialkylated tert-butyldiphenylamines, 2,3-di-hydro-3,3-dimethyl-4H-1,4-benzothiazine, phenothiazine, a mixture of mono- und dialkylated tert-butyl/tert-octylphenothiazines, a mixture of mono- und dialkylated tert-octylphenothiazines, N-allylphenothiazine, N,N,N',N'-tetraphenyl-1,4-diaminobut-2-ene, N,N-bis(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1.2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-($\alpha,\alpha$-dimethylbenzyl)-2'-hydroxyphenyl)benzotriazole, mixture of 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)-carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylthyl]-2'-hydroxyphenyl)benzotriazole, 2-(3'-dodecyl-2'-hydroxy-5'-methylphenyl)benzotriazole, and 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazol-2-ylphenol]; the transesterification product of 2-[3'-tert-butyl-5'-(2-methoxycarbonylethyl)-2'-hydroxyphenyl]-2H-benzotriazole with polyethylene glycol 300; [R—CH$_2$CH$_2$—COO(CH$_2$)$_3$]$_2$, where R=3'-tert-butyl-4'-hydroxy-5'-2H-benzotriazol-2-ylphenyl.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tertbutylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl $\alpha$-cyano-$\beta,\beta$-diphenylacrylate, isooctyl $\alpha$-cyano-$\beta,\beta$-diphenylacrylate, methyl $\alpha$-carbomethoxycinnamate, methyl $\alpha$-cyano-$\beta$-methyl-p-methoxy-cinnamate, butyl $\alpha$-cyano-$\beta$-methyl-p-methoxy-cinnamate, methyl $\alpha$-carbomethoxy-p-methoxycinnamate and N-($\beta$-carbomethoxy-$\beta$-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, the condensate of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-ectyloxy-2,2,6,6-tetramethylpiperidyl)succinate, the condensate of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-bis(4-n-butylamino-1,2,2,6,6-pentamethylpiperidyl)-1,3,5-triazine and 1,2-bis-(3-aminopropylamine)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, a mixture of 4-hexadecyloxy and 4-stearyloxy-2,2,6,6-tetramethylpiperidine, a condensation product of N,N'-bis-(2,2,6,6-tetramethyl-4-piperidyl) hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro[4,5]decane, a reaction product of 7,7,9,9-tetramethyl-2- cycloundecyl-1-oxa-3,8-diaza-4-oxospiro[4,5]decane und epichlorohydrin.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and the mixture thereof with 2-ethoxy-2'-ethyl-5,4'-di-tert-butoxanilide and mixtures of ortho- and para-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4-dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxy/tridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy)phenyl]-1,3,5-triazine, 2-(2-hydroxyphenyl)-4-(4-methoxyphenyl)-6-phenyl-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl)phosphite, trilauryl phosphite, trioctadecyl phosphite, distearyl pentaerythritol diphosphite, tris(2,4-di-tert-butylphenyl)phosphite, diisodecyl pentaerythritol diphosphite, bis(2,4-di-tert-butylphenyl) pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy- 2,4,8,10-tetra-tert-butyl-12H-dibenzo[d,g]-1,3,2-dioxaphosphocine, 6-fluoro-2,4,8,10-tetra-tert-butyl-12-methyldibenzo[d,g]-1,3,2-dioxaphosphocin, bis(2,4-di-tert-butyl-6-methylphenyl) methylphosphite, bis(2,4-di-tert-butyl-6-methylphenyl) ethylphosphite.

5. Hydroxylmines, for example, N,N-dibenzylhydroxylamine, N,N-diethylhydroxyl-amine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylmine derived from hydrogenated tallow amine.

6. Nitrones, for example N-benzyl-alpha-phenyl-nitrone, N-ethyl-alpha-methyl-nitrone, N-octyl-alpha-heptyl-nitrone, N-lauryl-alpha-undecyl-nitrone, N-tetradecyl-alpha-tridecyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-hepta-decyl-alpha-heptadecyl-nitrone, N-octadecyl-alpha-hexadecyl-nitrone, nitzone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, e.g. calcium stearate, zinc stearate, magnesium behenate, magnesium stearate, sodium ricinoleate and potassium palmitate, antimony pyrocatecholate or tin pyrocatecholate.

11. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers ("ionomers").

12. Fillers and reinforcing agents, for example, calcium carbonate, silicates, glass fibres, glass beads, asbestos, talc, kaolin, mica, barium sulfate, metal oxides and hydroxides, carbon black, graphite, sawdust or fibers of other natural products, synthetic fibers.

13. Other additives, for example, plasticisers, lubricants, emulsifiers, pigments, rheology additives, catalysts, flow-control agents, fluorescent whitening agents, flame-proofing agents, antistatic agents and blowing agents.

14. Benzofuranones and indolinones, for example those disclosed in U.S. Pat. No. 4,325,863, U.S. Pat. No. 4,338,244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 or EP-A-0 591 102 or 3-[4-(2-acetoxyethoxy)phenyl]-5,7-di-tert-butylbenzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]-phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one.

With the exception of the benzofuranones listed in item 14, the costabilisers are added typically in concentrations of 0.01 to 10%, based on the total weight of the material to be stabilised.

Further preferred compositions comprise, besides component (a) and the compounds of formula I, further additives, preferably phenolic antioxidants, light stabilisers and/or processing stabilisers.

Particularly preferred additives are phenolic antioxidants (item 1 in the list), sterically hindered amines (item 2.6 in the list), phosphites and phosphonites (item 4 in the list) and peroxide scavengers (item 8 in the list).

Further additives (stabilisers) which are also particularly preferred are benzofuran-2-ones, such as those disclosed, inter alia, in U.S. Pat. No. 4,325,863, U.S. Pat. No. 4,338, 244, U.S. Pat. No. 5,175,312, U.S. Pat. No. 5,216,052, U.S. Pat. No. 5,252,643, DE-A-4 316 611, DE-A-4 316 622, DE-A-4 316 876, EP-A-0 589 839 and EP-A-0 591 102.

Examples of such benzofuran-2-ones are compounds of formula

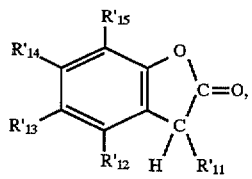

wherein $R'_{11}$ is an unsubstituted or substituted carbocyclic or heterocyclic aromatic ring system;

$R'_{12}$ is hydrogen;

$R'_{14}$ is hydrogen, alkyl of 1 to 12 carbon atoms, cyclopentyl, cyclohexyl or chloro;

$R'_{13}$ has the meaning of $R'_{12}$ or $R'_{14}$ or is a radical of formula

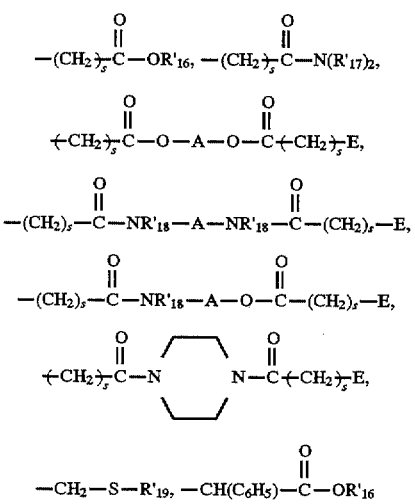

or —D—E, wherein $R'_{16}$ is hydrogen, alkyl of 1 to 18 carbon atoms, alkyl of 2 to 18 carbon atoms which is interrupted by oxygen or sulfur, dialkylaminoalkyl having a total of 3 to 16 carbon atoms, cyclopentyl, cyclohexyl, phenyl or phenyl which is substituted by 1 to 3 alkyl radicals having a total of at most 18 carbon atoms;

s is 0, 1 or 2;

substituents $R'_{17}$ are each independently of one another hydrogen, alkyl of 1 to 18 carbon atoms, cyclopentyl, cyclohexyl, phenyl; phenyl which is substituted by 1 or 2 alkyl radicals having a total of at most 16 carbon atoms, a radical of formula —$C_2H_4OH$, —$C_2H_4$—O—$C_tH_{2t+1}$ or

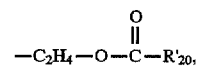

or, together with the linking nitrogen atom, form a piperidine or morpholine radical;

t is 1 to 18;

$R'_{20}$ is hydrogen, alkyl of 1 to 22 carbon atoms, or cycloalkyl of 5 to 12 carbon atoms;

A is alkylene of 2 to 22 carbon atoms which may be interrupted by nitrogen, oxygen or sulfur;

$R'_{18}$ is hydrogen, alkyl of 1 to 18 carbon atoms, cyclopentyl, cyclohexyl, phenyl; phenyl which is substituted by 1 or 2 alkyl radicals having a total of at most 16 carbon atoms, or benzyl;

$R'_{19}$ is alkyl of 1 to 18 carbon atoms;

D is —O—, —S—, —SO—, —$SO_2$— or —$C(R'_{21})_2$—;

substituents $R'_{21}$ are each independently of one another hydrogen, $C_1$–$C_6$alkyl, the two $R'_{21}$ radicals together containing 1 to 16 carbon atoms, and $R'_{21}$ is furthermore phenyl or a radical of formula

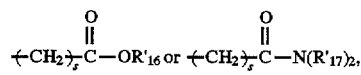

wherein s, $R'_{16}$ and $R'_{17}$ are as defined above;

E is a radical of formula

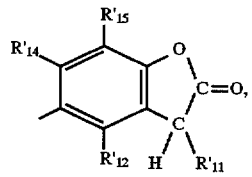

wherein $R'_{11}$, $R'_{12}$ and $R'_{14}$ are as deemed above; and $R'_{15}$ is hydrogen, alkyl of 1 to 20 carbon atoms, cyclopentyl, cyclohexyl, chloro, or a radical of formula

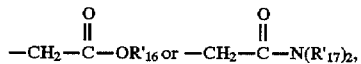

wherein $R'_{16}$ and $R'_{17}$ are as defined above, or $R'_{15}$ and $R'_{14}$, taken together, form a tetramethylene radical.

Preferred benzofuran-2-ones are those wherein $R'_{13}$ is hydrogen, alkyl of 1 to 12 carbon atoms, cyclopentyl, cyclohexyl, chloro or a radical of formula

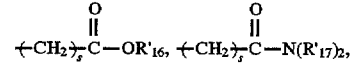

or —D—E, wherein s, $R'_{16}$, $R'_{17}$, D and E are as defined above, and $R'_{16}$ is preferably hydrogen, alkyl of 1 to 18 carbon atoms, cyclopentyl or cyclohexyl.

Preferred benzofuran-2-ones are also those wherein $R'_{11}$ is phenyl or phenyl which is substituted by 1 or 2 alkyl radicals having a total of at most 12 carbon atoms; $R'_{12}$ is hydrogen; $R'_{14}$ is hydrogen or alkyl of 1 to 12 carbon atoms; $R'_{13}$ is hydrogen, alkyl of 1 to 12 carbon atoms,

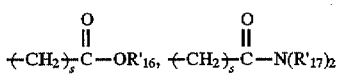

or —D—E; R'$_{15}$ is hydrogen, alkyl of 1 to 20 carbon atoms,

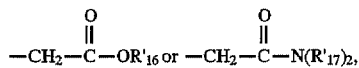

or R'$_{15}$ and R'$_{14}$, taken together, form a tetramethylene radical, in which groups s, R'$_{16}$, R'$_{17}$, D and E are as defined at the outset.

Particularly interesting benzofuran-2-ones are also those wherein R'$_{13}$ is hydrogen, alkyl of 1 to 12 carbon atoms or —D—E; R'$_{12}$ and R'$_{14}$ are each independently of the other hydrogen or alkyl of 1 to 4 carbon atoms; R'$_{15}$ is alkyl of 1 to 20 carbon atoms, and D and E are as defined at the outset.

Of particular interest are finally also those benzofuran-2-ones, wherein R'$_{13}$ is alkyl of 1 to 4 carbon atoms or —D—E; R'$_{12}$ and R'$_{14}$ are hydrogen; R'$_{15}$ is alkyl of 1 to 4 carbon atoms, cyclopentyl or cyclohexyl, D is a —C(R'$_{21}$)$_2$— group, and E is a radical of formula

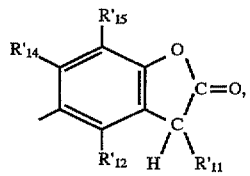

the substituents R'$_{21}$ being identical or different and are each alkyl of 1 to 4 carbon atoms, and R'$_{11}$, R'$_{12}$, R'$_{14}$ and R'$_{15}$ are as defined above.

The amount of benzofuran-2-ones additionally employed can vary within wide limits. The novel compositions may typically contain them in amounts of 0.0001 to 5% by weight, preferably of 0.001 to 2% by weight, most preferably of 0.01 to 2% by weight.

The compounds of formula I and any further additives are incorporated into the polymeric organic material by known methods, typically before or during shaping or alternatively by applying the dissolved or dispersed compounds to the polymeric organic material, with subsequent evaporation of the solvent, when used. The compounds of formula I can also be added to the materials to be stabilised in the form of a masterbatch which contains these compounds in a concentration of typically 2.5 to 25% by weight.

The compounds of formula I can also be added before or during polymerisation or before crosslinking.

The compounds of formula I can be incorporated into the material to be stabilised in pure form or encapsulated in waxes, oils or polymers.

The compounds of formula I can also be sprayed onto the polymer to be stabilised. They are able to dilute other additives (e.g. the conventional additives mentioned above) or their melts, so that they can also be sprayed onto the polymer to be stabilised together with these additives. Application by spraying during deactivation of the polymerisation catalysts is particularly advantageous, in which case the steam used for the deactivation may be used for spraying.

In the case of spherically polymerised polyolefins, the compounds of formula I may be usefully applied by spraying, if desired together with other additives.

The materials stabilised in this manner can be used in a very wide range of forms, typically including sheets, filaments, ribbons moulded articles, profiles or as binders for paints, adhesives or putties.

As already mentioned, the organic materials to be protected are preferably organic polymers, more particularly synthetic polymers. It is especially useful to protect thermoplastic materials and, preferably, polyolefins. To be highlighted in this connection is in particular the excellent action of the compounds of formula I as processing stabilisers (heat stabilisers). For this purpose, they are usefully added to the polymer before or during processing. However, other polymers (e.g. elastomers) or lubricants or hydraulic fluids can also be stabilised against degradation, such as light-induced or thermal oxidalive degradation Examples of elastomers will be found in the above list of possible organic materials.

Suitable lubricants and hydraulic fluids may be based on mineral or synthetic oils, or mixtures thereof. The lubricants are known to the person skilled in the art and are described in the relevant technical literature, for example in Dieter Klamann, "Schmierstoffe und verwandte Produkte" (Verlag Chemie, Weinheim, 1982), in Schewe-Kobek, "Das Schmiermittel-Taschenbuch" (Dr. Alfred Hüthig-Verlag, Heidelberg, 1974) and in "Ullmanns Enzyklopädie der technischen Chemie", Vol. 13, pages 85–94 (Verlag Chemie, Weinheim, 1977).

Accordingly, a preferred embodiment of this invention is the use of compounds of formula I for stabilising organic materials against oxidative, thermal or light-induced degradation.

The novel compounds of formula I are distinguished by their markedly good stability to hydrolysis and their advantageous colour behaviour, i.e. minor discoloration of the organic materials during processing.

Organic materials stabilised with the novel compounds are particularly well protected against light-induced degradation.

Accordingly, the invention also relates to a process for stabilising an organic material against oxidative, thermal or light-induced degradation, which process comprises incorporating in, or applying to, said material at least one compound of formula I.

The following Examples illustrate the invention more fully. Parts and percentages are by weight.

EXAMPLE 1

Preparation of Compound (101) (Table 1)

10.12 g (25.0 mmol) of 2,10-dimethyl-4,8-di-tert-butyl-6-chloro-12H-dibenzo[d,g][1,3,2]-dioxaphosphocine [GB-A-2 250 990, Example 1a, page 17], 10.5 ml (75.0 mmol) of triethylamine and 100 ml of toluene are charged at room temperature and under nitrogen to a 350 ml sulfonation flask. With stirring, a solution of 4.26 g (25.0 mmol) of 4-amino-1,2,2,6,6-pentamethylpiperidine [Beilstein EII, Vol. 22, page 321 (1953)] in 30 ml of toluene is added dropwise to this suspension. The reaction mixture is refluxed for 2 hours, then cooled to room temperature and filtered. The filtrate is concentrated on a vacuum rotary evaporator. Crystallisation of the residue from hexane yields 7.7 g (57%) of 2,10-dimethyl-6-(1,2,2,6,6-pentamethylpiperidin-4-ylamino)-4,8-di-tert-butyl-12H-dibenzo-[d,g][1,3,2] dioxaphosphocine (57%) (compound (101)) as a white powder, m.p. 207°–216° C. Analysis: calcd: C 73.57%; H 9.54%; N 5.19%; found: C 74.38%; H 10.03%; N 4.68%.

In analogy to Example 1, compounds (102), (103) and (104) (Table 1) are obtained starting from the corresponding cyclic chlorophosphite derivative, typically 2,4,8,10-tetra-tert-butyl-6-chloro-dibenzo[d,f][[1,3,2]dioxaphocine

[EP-A-0 569 328, Example 1, page 10], 2,4,8,10-tetra-tert-butyl-6-chloro-12H-dibenzo[d,g][1,3,2]dioxaphosphocine [GB-A-2 087 399, Example A, page 8] or 2,4,8,10-tetra-tert-butyl-6-chloro-12-methyl-12H-dibenzo[d,g][1,3,2] dioxaphosphocine [EP-A-0 540 025, Example A, page 7], with 4-amino-1,2,2,6,6-pentamethylpiperidine.

TABLE 1

| Cmpd | $R_1$ | $R_2$ | X | m.p. °C. | C (%), H (%), N (%) (calcd/found) | $^{31}$P-NMR (145.78 MHz) (ppm) |
|---|---|---|---|---|---|---|
| 101 | tert-butyl | methyl | —CH$_2$— | 207–216 | 73.57 9.54 5.19<br>74.38 10.03 4.68 | 143.11 |
| 102 | tert-butyl | tert-butyl | — | 205–210 | 74.96 10.10 4.60<br>75.02 10.17 4.25 | 148.38 |
| 103 | tert-butyl | tert-butyl | —CH$_2$— | 206–214 | 75.20 10.19 4.50<br>75.40 10.12 4.40 | 142.47 |
| 104 | tert-butyl | tert-butyl | —CH(CH$_3$)— | 226–236 | 75.43 10.29 4.40<br>75.26 10.22 4.22 | 141.92 |

EXAMPLE 2

Stabilisation of Multiple-Extruded Polypropylene 1.3 kg of polypropylene powder (Profax® 6501), which has been prestabilised with 0.025 % of Irganox® 1076 (n-octadecyl (3-[3,5-di-tert-butyl-4-hydroxyphenyl] propionate] (melt flow index 3.2 measured at 230°/2.16 kg), are blended with 0.05% of Irganox® 1010 (pentaerythrityl tetrakis-[3-(3,5-di-tert-butyl-4-hydroxyphenyl)propionate), 0.05% of calcium stearate, 0.03% of dihydrotalcite [DHT 4A®, Kyowa Chemical Industry Co., Ltd., Mg$_{4.5}$Al$_2$(OH)$_{13}$CO$_3$·3,5 H$_2$O] and 0.05% of the compound of Table 1. This blend is then extruded in an extruder having a cylinder diameter of 20 mm and a length of 400 mm at 100 rpm, the 3 heating zones being adjusted to the following temperatures: 260° C., 270° C. and 280° C. The extrudate is cooled by drawing it through a water bath and is then granulated. This granulate is repeatedly extruded. After 3 extrusions, the melt flow index is measured at 230° C./2.16 kg). A substantial increase in the melt index denotes pronounced chain degradation, i.e. poor stabilisation. The results are shown in Table 2.

TABLE 2

| Compound of Table 1 | Melt index after 3 extrusions |
|---|---|
| — | 20.0 |
| 101 | 6.0 |
| 102 | 6.2 |
| 103 | 6.3 |
| 104 | 6.6 |

What is claimed is:

1. A compound of formula I

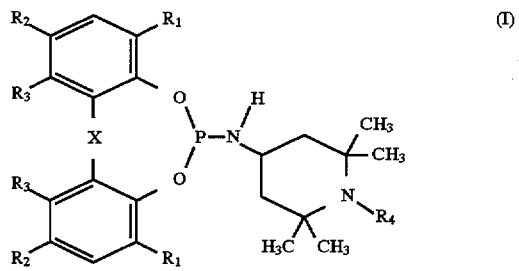

wherein

X is a direct bond, sulfur or —CHR$_5$—,

R$_1$ is hydrogen, C$_1$–C$_{25}$alkyl, unsubstituted or C$_1$–C$_4$alkyl-substituted C$_5$–C$_8$cycloalkyl; unsubstituted or C$_1$–C$_4$alkyl-substituted C$_5$–C$_8$cycloalkenyl; unsubstituted or C$_1$–C$_4$alkyl-substituted phenyl; C$_7$–C$_9$phenylalkyl or —CH$_2$—S—R$_6$, R$_2$ is hydrogen, C$_1$–C$_{25}$alkyl, C$_2$–C$_{24}$alkenyl, unsubstituted or C$_1$–C$_4$alkyl-substituted C$_5$–C$_8$cycloalkyl; unsubstituted or C$_1$–C$_4$alkyl-substituted C$_5$–C$_8$cycloalkenyl; unsubstituted or C$_1$–C$_4$alkyl-substituted phenyl; C$_7$–C$_9$-phenylalkyl or —CH$_2$—S—R$_6$, R$_3$ is hydrogen or methyl, R$_4$ is C$_1$–C$_8$alkyl, O˙, OH, NO, —CH$_2$CN, C$_1$–C$_{18}$alkoxy, C$_5$–C$_{12}$cycloalkoxy, C$_3$–C$_6$-alkenyl, C$_3$–C$_6$alkynyl, C$_1$–C$_8$acyl, C$_7$–C$_9$phenylalkyl which is unsubstituted or substituted at the phenyl ring by C$_1$–C$_4$alkyl, R$_5$ is hydrogen or C$_1$–C$_8$alkyl, and R$_6$ is C$_1$–C$_{20}$alkyl.

2. A compound according to claim 1, wherein $R_1$ is hydrogen, $C_1$–$C_8$alkyl, $C_5$–$C_8$cycloalkyl, $C_5$–$C_8$cycloalkenyl, phenyl, $C_7$–$C_9$phenylalkyl or —$CH_2$—S—$R_6$, $R_2$ is hydrogen, $C_1$–$C_{18}$alkyl, $C_2$–$C_{18}$alkenyl, $C_5$–$C_8$cycloalkyl, $C_5$–$C_8$cycloalkenyl, phenyl, $C_7$–$C_9$phenylalkyl or —$CH_2$—S—$R_6$, $R_4$ is $C_1$–$C_4$alkyl, $C_4$–$C_{18}$alkoxy, $C_5$–$C_8$cycloalkoxy, allyl, propargyl, acetyl or benzyl, $R_5$ is hydrogen or $C_1$–$C_6$alkyl, and $R_6$ is $C_1$–$C_{12}$alkyl.

3. A compound according to claim 1, wherein $R_1$ and $R_2$ are each independently of the other hydrogen, $C_1$–$C_{12}$alkyl, cyclohexyl, phenyl or benzyl.

4. A compound according to claim 1, wherein $R_4$ is $C_1$–$C_4$alkyl, $C_4$–$C_{18}$alkoxy, $C_5$–$C_8$cycloalkoxy, allyl, propargyl, acetyl or benzyl.

5. A compound according to claim 1, wherein $R_4$ is $C_1$–$C_4$alkyl.

6. A compound according to claim 1, wherein

X is a direct bond or —$CHR_5$, $R_1$ is $C_1$–$C_4$alkyl, cyclohexyl or phenyl, $R_2$ is $C_1$–$C_4$alkyl, cyclohexyl or phenyl, $R_3$ is hydrogen, $R_4$ is $C_1$–$C_4$alkyl, allyl or benzyl, and $R_5$ is hydrogen or $C_1$–$C_4$alkyl.

7. A compound according to claim 1, wherein

X is a direct bond or —$CHR_5$, $R_1$ is $C_1$–$C_4$alkyl, $R_2$ is $C_1$–$C_4$alkyl, $R_3$ is hydrogen, $R_4$ is methyl, and $R_5$ is hydrogen or methyl.

8. A composition comprising
   a) an organic material susceptible to oxidative, thermal or light-induced degradation, and
   b) at least one compound of formula I according to claim 1.

9. A composition according to claim 8, comprising further additives in addition to the components (a) and (b).

10. A composition according to claim 9, wherein the further additives are phenolic antioxidants, light stabilisers or/and processing stabilisers.

11. A composition according to claim 9, wherein the further additive is at least one compound of the benzofuran-2-one type.

12. A composition according to claim 8, wherein component a) is a natural, semi-synthetic or synthetic polymer.

13. A composition according to claim 8, wherein component (a) is a thermoplastic polymer.

14. A composition according to claim 8, wherein component (a) is a polyolefin.

15. A composition according to claim 8, wherein component (a) is polyethylene or polypropylene.

16. A composition according to claim 8, which contains component (b) in an amount of 0.01 to 10%, based on the weight of component (a).

17. A process for the stabilisation of an organic material against oxidative, thermal or light-induced degradation, which process comprises incorporating in, or applying to, said material at least one compound of formula I as defined in claim 1.

18. A process for the preparation of a compound of formula I according to claim 1, which comprises reacting a compound of formula II

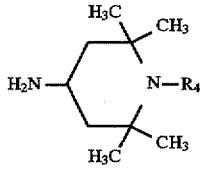

wherein $R_4$ is as defined in claim 1, with a cyclic halophosphite of formula III

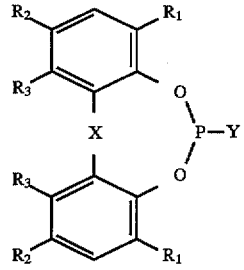

wherein X, $R_1$, $R_2$ and $R_3$ are as defined in claim 1, and Y is chloro, bromo or iodo.

* * * * *